US005507135A

United States Patent [19]

Grönberg et al.

[11] Patent Number: 5,507,135

[45] Date of Patent: Apr. 16, 1996

[54] APPARATUS FOR TREATING SPINAL DISORDERS OF AN ANIMAL PARTICULARLY THOSE OF A HORSE

[76] Inventors: Pauli Grönberg, Koskitie 11 FIN-04300, Tuusula; Hannes Karppinen, Yrttimaantie 36, FIN-00479, Helsinki, both of Finland

[21] Appl. No.: 211,416

[22] PCT Filed: Oct. 1, 1992

[86] PCT No.: PCT/FI92/00256

§ 371 Date: Jul. 22, 1994

§ 102(e) Date: Jul. 22, 1994

[87] PCT Pub. No.: WO93/06788

PCT Pub. Date: Apr. 15, 1993

[30] Foreign Application Priority Data

Jan. 20, 1991 [FI] Finland .................................... 914634

[51] Int. Cl.[6] .................................................... A61F 5/00

[52] U.S. Cl. ................................................ 54/1; 606/237

[58] Field of Search ................................ 54/1, 37.1, 40.1, 54/71; 606/54, 237, 240; 119/814

[56] References Cited

U.S. PATENT DOCUMENTS

| | | | |
|---|---|---|---|
| 845,558 | 2/1907 | Lee | 54/1 |
| 1,747,702 | 2/1913 | Gilbert | 119/814 |
| 1,759,514 | 5/1930 | Loose . | |
| 2,447,698 | 8/1948 | Haberer . | |
| 2,593,624 | 4/1952 | Stevens | 606/237 |
| 2,835,247 | 5/1958 | Stabholc . | |
| 2,970,592 | 2/1961 | David . | |
| 3,926,182 | 12/1975 | Stabholz . | |

FOREIGN PATENT DOCUMENTS

| | | | |
|---|---|---|---|
| 2403534A | 8/1974 | Germany . | |
| 958549 | 5/1964 | United Kingdom | 119/814 |

*Primary Examiner*—Robert P. Swiatek
*Attorney, Agent, or Firm*—Ronald J. Kubovcik

[57] ABSTRACT

An apparatus and method for treating spinal disorders in an animal, particularly a horse. The apparatus includes a pair of elongated support plates arranged in an opposing relationship. A frame having a hole therethrough is mounted above the support plates. The frame is oriented so that the hole therethrough defines an axis extending between the support plates. A rod is disposed in the hole in the frame, the lower end of the rod being movable toward and away from the frame along the axis and the rod being rotatable about the axis. A fork-shaped element having a pair of adjustable pegs arranged in an opposing relationship is attached to the lower end of the rod. A harness attached to the support plates is used to mount the support plates on the animal. The method includes the steps of disposing the fork-shaped element above a portion of a spine of an animal, lowering the fork-shaped element so that it contacts the portion of the spine, adjusting the pegs of the fork-shaped element so that the pegs are situated at opposing sides of the portion of the spine, and moving the fork-shaped element to align the portion of the spine.

12 Claims, 1 Drawing Sheet

Figure 1:
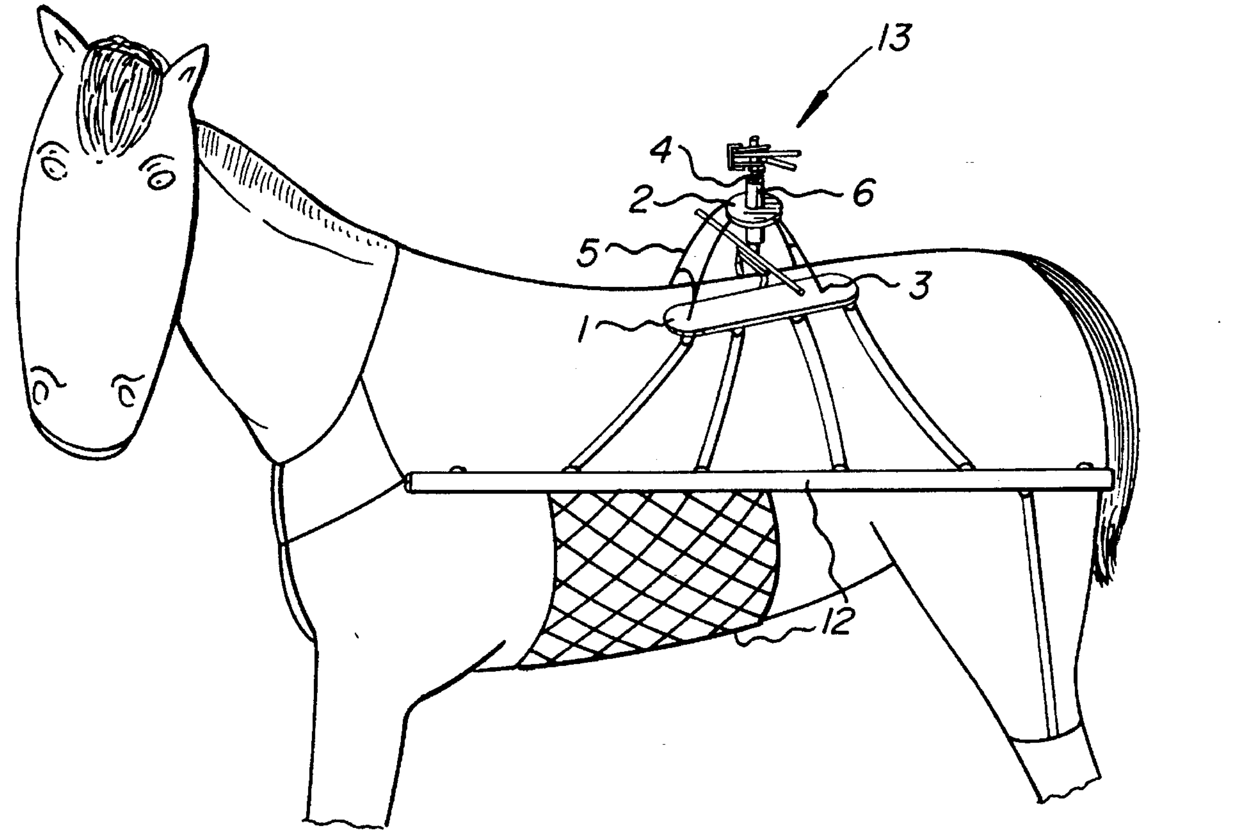

APPARATUS FOR TREATING SPINAL DISORDERS OF AN ANIMAL PARTICULARLY THOSE OF A HORSE

The present invention concerns an apparatus for treating spinal disorders of an animal particularly those of a horse, said apparatus comprising fixing means such as a strappable harness or belts suited for mounting the apparatus on the animal's back and a fork-shaped element acting on the back.

Horses in particular are subject to spinal disorders. Such disorders are typically evidenced as a certain type of limping and changes in the gait. The horse may shorten its gait, poorly distributes the weight on its legs or hesitate to flex its back when running in the bends. A spinal disorder lowers the horse's performance.

The horse's spine has above and below strong, large muscles that may rupture in motion. The spine is formed by vertebrae whose processes rise higher from the spine as can be felt by moving a hand over the horse's back along points where the tips of the processes are thicker. Adjacent vertebral processes can cause compression of nerves leaving the sacral canal through the intervertebral foramina, whereby pain occurs at the flexing of the back. Due to the thickness of the spinal muscles, conventional radiographic examination of the spine fails to provide sharp images even if the horse is anaesthetized. The radiographic examination reveals only major changes such as fractures and ruptures, not any lesser changes in the vertebrae themselves.

Spinal disorders are conventionally treated by rest, and occasionally, by drugs administered to the horse. Small changes in the vertebrae can possibly be mended surgically to relieve compression on the nerve roots. In the case of a chronic disorder in the region of the sacrum and ileum, rest will be of little help; rather, the horse should be rehabilitated by a stepwise more arduous schedule of training, thereby strengthening the rear trunk muscles supporting the spine. Obviously, a great number of different approaches are available for treating spinal disorders with varying results.

It is an object of the present invention to achieve an apparatus suited for treating a certain category of spinal disorders. These disorders include those causing muscular tension and spasms. The apparatus serves to the end of relaxing such muscular tensions. The apparatus according to the invention is characterized in that the fork-shaped element is adapted movable in a direction essentially perpendicular to the animal's back and that the apparatus further incorporates a rotatable element with which the fork-shaped element is rotated about the axis essentially perpendicular to the back and is simultaneously pressed against the back.

A preferred embodiment of the invention is characterized in that the rotatable element comprises manually rotatable lever arms connected to the fork-shaped element.

Another embodiment of the invention is characterized in that, for the purpose of moving the fork-shaped element with respect to the apparatus in the direction perpendicular to the spine, a metal rod is connected to the fork-shaped element so as to be movable within a pipe incorporated in the device and, for the purpose of transferring the rod toward the spine, said metal rod is complemented with a mechanism triggerable by a quick-release latch after the transfer operation.

A further embodiment of the invention is characterized in that the fork-shaped element is rotatable by means of the metal rod about the rod axis oriented perpendicular to the animal's back.

The apparatus according to the invention can be applied for treating the following objects: cervical vertebrae, thoracic vertebrae, lumbar vertebrae, sacral vertebrae, caudal vertebrae, atlas, axis, etc. Treatment by the apparatus relieves nerve rami from compression and muscles from tension; the treatment enhances blood circulation and removes stresses imposed on articulating facets and lamina, thus allowing the tissues to recover rapidly from loads caused by incorrect posture. Further, the apparatus can be used for applying manipulating treatment on tens of acupuncture, shiatsu and other sensitive points communicating widely around the nervous network. The apparatus can be employed for relaxing painful spasms and single-sided tensions and reflected nerve pains.

Figure 2:
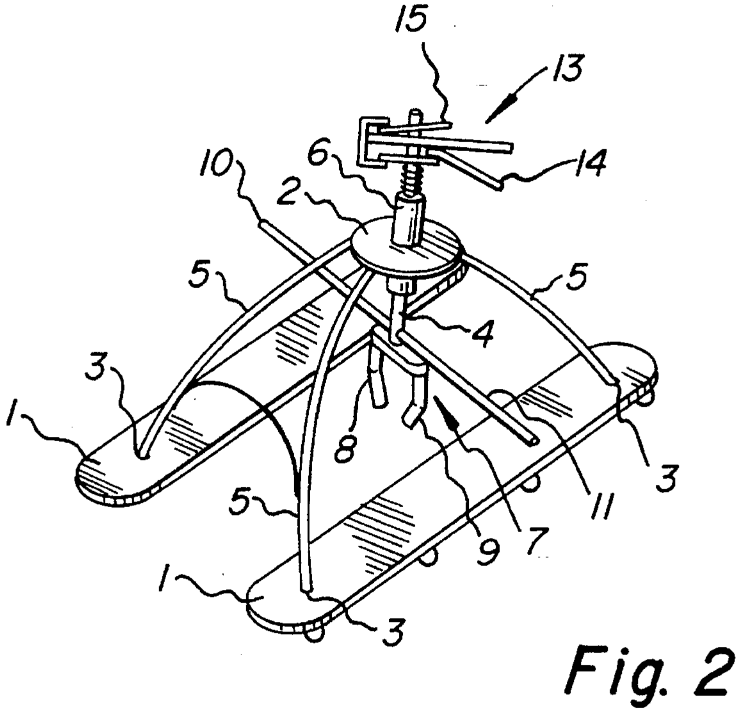

In the following, the invention will be examined in more detail by means of the preferred exemplifying embodiments with reference to the attached drawing, in which FIG. 1 shows an apparatus according to the invention mounted on the back of a horse, FIG. 2 shows the apparatus according to the invention in a larger scale.

In FIG. 1 the apparatus according to the invention is mounted on a horse's back. Horse acts herein only as an exemplifying animal. The apparatus can equally well be used in the treatment of any vertebrate animal, even man. The apparatus is mounted on the horse's back in this exemplifying embodiment by means of a strappable harness 12 as shown in FIG. 1. The actual structure of the harness or other fixing arrangements is nonessential. The only important requirement is that the apparatus must stay firmly fixed during the entire treatment.

The body of the apparatus in the illustrated embodiment comprises a metal frame 2 and metal arcs 5 attached to it. The lower ends of the metal arcs carry at points 3 pivotally mounted support plates 1 the number of which is two: one on each side of the horse's spine. The above-mentioned mounting harness 12 is further attached to said support plates 1.

Essentially to the center of the frame 2 of the apparatus is made a hole to accommodate the mounting of a metal pipe 6 or similar tubular element. Through the pipe is inserted an iron rod 4 which is movable toward and retractable from the horse's back. To the lower end of the iron rod 4 is attached a fork-shaped element 7 acting on the horse's back, said element comprising two essentially identical, in this case blunt pegs 8, 9. The pegs or at least their tips are movable at a closer or wider mutual distance. For this purpose, an adjustment mechanism is adapted not illustrated in the drawing to a greater detail. Any competent craftsman familiar with mechanism constructions can easily devise such adjustment means. The reason for the need to move the pegs 8, 9 is the requirement of correct mutual distance and position adjustment on the horse's back prior to the actual treatment.

The apparatus further comprises lever arm or arms 10, 11 which advantageously are detachable. This property is implemented by, e.g., providing the iron bar 4 with threaded holes into which the lever arms 10, 11 are inserted by screwing. Obviously, any suitable construction of the lever arm is possible such as, e.g., a single straight bar passing through the iron rod 4. Advantageously, however, the lever arm is mounted closest possible to the fork-shaped element 7, whereby actual rotation operation about the iron rod 4 is more efficiently possible without causing unwanted lateral movements.

The apparatus according to the invention is mounted on the back of the animal suffering from a spinal disorder, a horse in the exemplifying case, with the help of the harness 12 so that the fork-shaped element 7 is aligned above the actual point of disorder or pain. After the straps of the harness are fitted and tightened and the apparatus is solidly fixed in place, the fork-shaped element 7 is lowered at the end of the iron rod 4 to rest against the back. At this stage the pegs 8, 9 are still kept maximally outdistanced from each other. When the fork-shaped element is vertically properly aligned above the correct point, the fork-shaped element is adjusted until the pegs 8, 9 are closed between the desired spinous processes. Next, the lever arm or arms 10, 11 are grabbed, a push and rotating movement is performed thus aligning the spinous processes in their correct positions, whereby the muscular spasms are relaxed.

Besides manually the push can be performed mechanically, in particular if muscles are stiff due to a spasm, because pressure cannot be applied steadily against the back by manual methods. One advantageous pressure applying mechanism is illustrated in the drawings. Thus, the iron bar 4 has a transfer mechanism 13 which can be implemented as, e.g., the advance and release mechanism known in the art from a putty cartridge ram pistol. In short, the downward pushing of the iron bar by means of this mechanism takes place by pressing the trigger 14 as many times as is necessary to achieve the desired depth. In this manner the transfer mechanism tightens the fork-shaped element 7 against the back for the duration of the treatment. The compressive pressure is released by tripping the mechanism by pressing the quick-release latch plate 15 at the completion of the treatment. This illustrated embodiment serves as an example of the multiple applications and constructions possible for the apparatus.

To those versed in the art it is evident that the scope of the invention is not exhausted by the exemplifying embodiments described above; instead, the invention can be varied within the disclosed claims. The constructional details of the apparatus can thus be varied widely. The essentials of the invention are, however, in that apparatus comprises strapping means allowing its solid mounting essentially immovably on the back; an element movable in a direction perpendicular to the back and acting on the back; and lever elements permitting the rotation of the element acting on the back.

What is claimed is:

1. An apparatus for treating spinal disorders in an animal, said apparatus comprising:

a pair of elongated support plates arranged in an opposing relationship;

a frame mounted above said support plates, said frame having a hole therethrough and being oriented so that said hole defines an axis extending between said support plates;

a rod disposed in said hole in said frame so that a first end of said rod is below said frame and a second end of said rod is above said frame, said first end of said rod being movable toward and away from said frame along said axis and said rod being rotatable about said axis;

a fork-shaped element attached to said first end of said rod; and a harness attached to said support plates for mounting said support plates on said animal.

2. The apparatus of claim 1, wherein said fork-shaped element has a pair of adjustable pegs arranged in an opposing relationship.

3. The apparatus of claim 2, wherein a lever arm is attached to said rod for rotating said rod about said axis.

4. The apparatus of claim 3, wherein said lever arm is attached to said rod proximate to said fork-shaped element.

5. The apparatus of claim 4, wherein said frame is mounted above said support plates by metal arcs pivotally connected to said support plates.

6. The apparatus of claim 3, wherein a tube is disposed in said hole in said frame, said rod is movably and rotatably disposed in said tube, and pressure means for driving said first end of said rod in a direction away from said frame is provided at said second end of said rod.

7. The apparatus of claim 1, wherein a tube is disposed in said hole in said frame, said rod is movably and rotatably disposed in said tube, and pressure means for driving said first end of said rod in a direction away from said frame is provided at said second end of said rod.

8. The apparatus of claim 7, wherein said pressure means for driving said first end of said rod in a direction away from said frame is provided with a latch plate for releasing said pressure means.

9. A method for treating spinal disorders in an animal, said method comprising the steps of:

disposing a fork-shaped element having a pair of adjustable pegs arranged in an opposing relationship above a spine of an animal;

lowering said fork-shaped element so that said fork-shaped element contacts said animal;

adjusting said pegs of said fork-shaped element so that said pegs are situated at opposing sides of a portion of said spine; and moving said fork-shaped element to align said portion of said spine.

10. The method of claim 9, wherein the step of moving said fork-shaped element to align said portion of said spine comprises simultaneously pushing said fork-shaped element toward said portion of said spine and rotating said fork-shaped element about an axis perpendicular to said portion of said spine.

11. The method of claim 10, wherein said animal is a horse.

12. The method of claim 9, wherein said animal is a horse.

* * * * *